United States Patent

Meehan et al.

[11] Patent Number: 5,865,729
[45] Date of Patent: Feb. 2, 1999

[54] APPARATUS FOR FACILITATING GYNECOLOGICAL EXAMINATIONS AND PROCEDURES

[75] Inventors: Alyce A. Meehan, Elmont; Shiro Bito, Commack, both of N.Y.

[73] Assignee: Olympus America, Inc., Melville, N.Y.

[21] Appl. No.: 948,876

[22] Filed: Oct. 10, 1997

[51] Int. Cl.⁶ .................................................. A61B 17/00
[52] U.S. Cl. .................. 600/207; 600/208; 600/235; 600/245
[58] Field of Search ................................. 600/184, 201, 600/207, 208, 212, 235, 245

[56] References Cited

U.S. PATENT DOCUMENTS

| | | | |
|---|---|---|---|
| 90,217 | 5/1869 | Alyworth | 600/184 |
| 118,683 | 9/1871 | Bruce | 600/184 |
| 2,548,602 | 4/1951 | Greenburg | 600/207 |
| 3,831,587 | 8/1974 | Boyd | 600/207 |
| 3,851,642 | 12/1974 | McDonald | 600/205 X |
| 4,946,440 | 8/1990 | Hall | 604/95 |
| 5,176,630 | 1/1993 | Shilling et al. | |
| 5,301,090 | 4/1994 | Hed | |
| 5,545,122 | 8/1996 | Spruill | |
| 5,716,329 | 2/1998 | Dieter | 600/184 X |
| 5,743,852 | 4/1998 | Johnson | 600/207 |

*Primary Examiner*—Jeffrey A. Smith
*Attorney, Agent, or Firm*—Michaelson & Wallace; Peter L. Michaelson; John C. Pokotylo

[57] ABSTRACT

A vaginal speculum having an inflatable bladder which includes a central channel and an inlet outlet port. The inflatable bladder may include optical fibers for illumination.

19 Claims, 9 Drawing Sheets

APPARATUS FOR FACILITATING GYNECOLOGICAL EXAMINATIONS AND PROCEDURES

BACKGROUND OF THE INVENTION a. Field of the Invention

The present invention concerns gynecological examinations and procedures. In particular, the present invention concerns instruments for facilitating the examination of, the treatment of, and the taking of samples from, the cervix and/or the uterus while minimizing patient discomfort.

b. Related Art

§1. BACKGROUND

§1.1. Purpose of Examination

Figure 1:
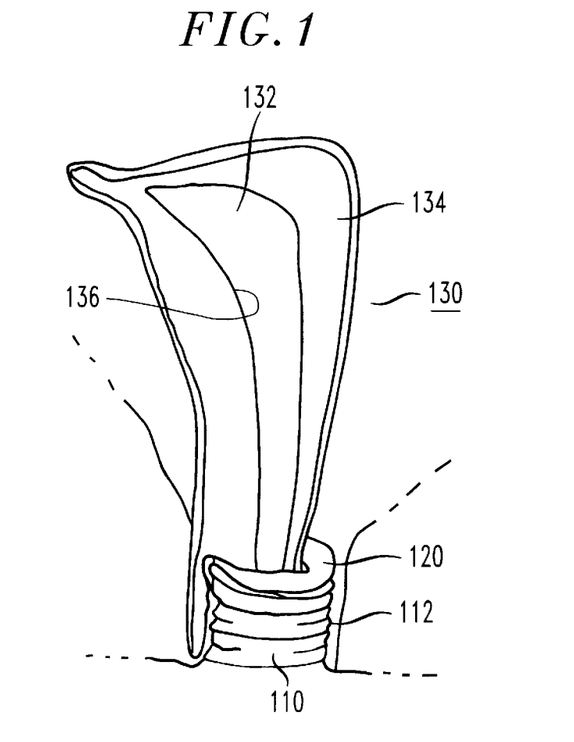
FIG. 1 is a partial cross-sectional illustration of a human vagina, cervix, and uterus.

Gynecologists often examine a woman's cervix or uterus. Referring to FIG. 1, the cervix 120 is located at the distal end of a vagina 110, and separates the vagina 110 from the uterus 130. The vagina walls 112 may obstruct the view of the cervix 120 from the proximal end of the vagina 110. As is known, the uterus 130 is a pear-shaped muscular organ which receives and holds fertilized ovum during the development of the fetus and serves to expulse the fetus at birth. The walls 136 of the uterus 130 define a void 132 surrounded by muscles 134.

A gynecologist may wish to visually inspect the cervix for discoloration and/or growths, particularly if their patient has a family history of cervical cancer. In addition to the visual inspection, the gynecologist may wish to take a sample biopsy of the cervical tissue or a mucosal biopsy. In addition, a gynecologist may wish to inspect the mucus lining or wall (the endometrium) 136 of the uterus 130, especially if his or her patient (a) is suffering from abnormal bleeding (in particular during pregnancy), (b) has had fertility problems, or (c) has a family history of cancer of the uterus. If his or her patient has an inter-uterary device (or "IUD") for birth control, the gynecologist may wish to monitor the status of the IUD.

To facilitate the examination and treatment of the cervix 120 or uterus 130, medical devices known as vaginal "specula" are often used by gynecologists. Various types of known vaginal specula, their use, and their disadvantages are discussed below.

§1.2 Structure of Vaginal Specula

Figure 7A:
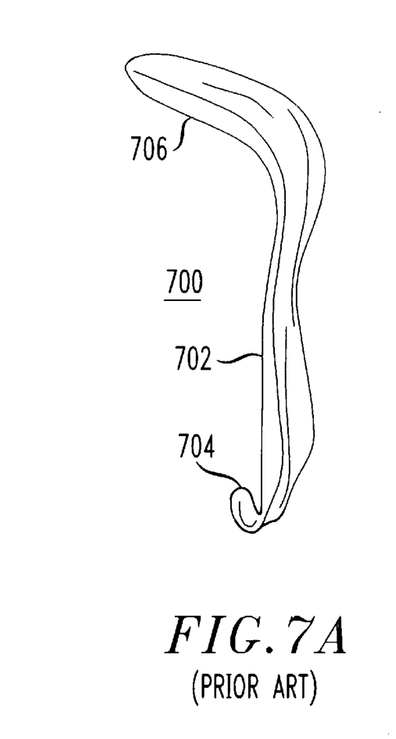
FIGS. 7a through 7d illustrate known vaginal specula.
Figure 7B:
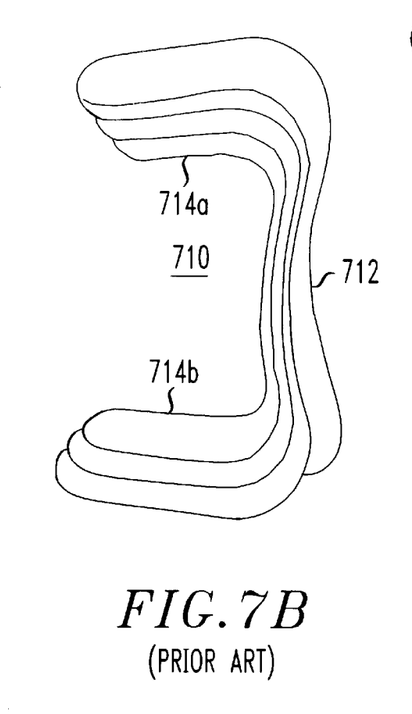
Figure 7C:
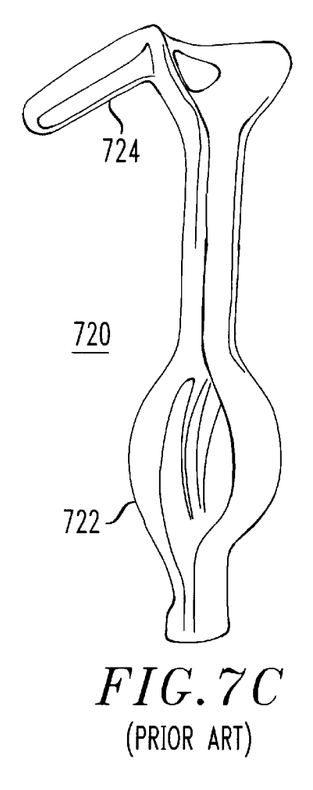
Figure 7D:
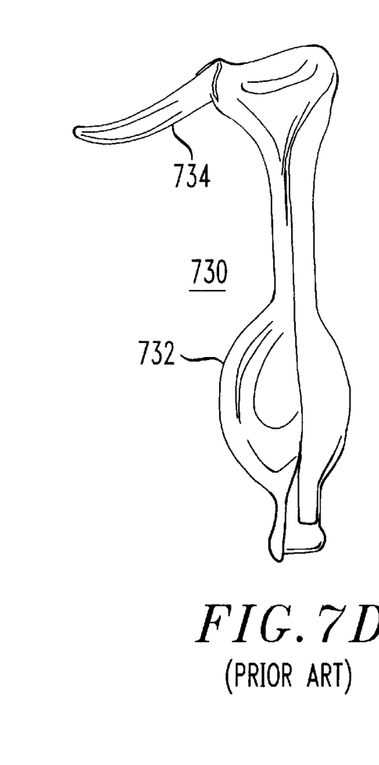

FIGS. 7a through 7d illustrate perspective views of various types of vaginal specula. Referring first to FIG. 7a, a vaginal speculum 700 includes a bill (or blade) portion 706 which is contoured to the shape of a portion of the vaginal wall 112, a section 702 for the gynecologist to hold, and a stop 704 against which the gynecologist may pull to separate the vaginal walls 112. FIG. 7b illustrates small medium and large double ended 714a/714b vaginal specula 710. In each case, the vaginal speculum 710 includes a section 712 between the two bills (or blades) 714a and 714b. Referring now to FIG. 7c, the vaginal speculum 720 includes a weighted area 722 and a slightly angled bill (or blade) 724. Similarly, referring to FIG. 7d, the vaginal speculum 730 includes a weighted area 732 and a slightly angled and curved bill (or blade) 734. The combination of the weight 722/732 and the angled bill (or blade) 724/734 permits the gynecologist to free their hands, at least for a short period of time, since the weight of the speculum will pull down on the section of the vaginal wall 112 in contact with the bill (or blade) 724/734 and the angle of the bill (or blade) 724/734 should prevent the speculum from slipping out of the vagina 110. All of the vaginal specula shown in FIGS. 7a through 7d permit one side of the vaginal wall 712 to be pulled. These vaginal specula may suffice for visually examining a portion of the vaginal wall 112 or the cervix 120, but may be insufficient for inspecting and taking samples from the cervix 120 and/or uterus 130.

Figure 8A:
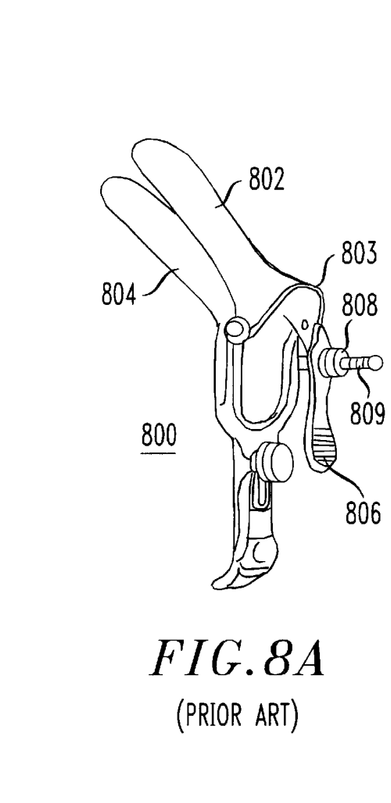
FIGS. 8a through 8d illustrate known double bladed or double billed vaginal specula.
Figures 8B, 8C:
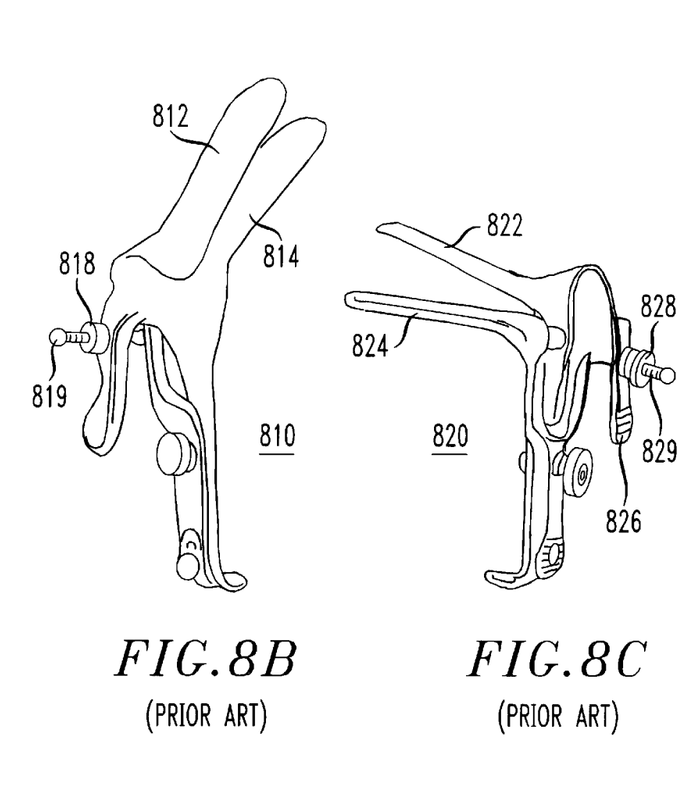
Figure 8D:
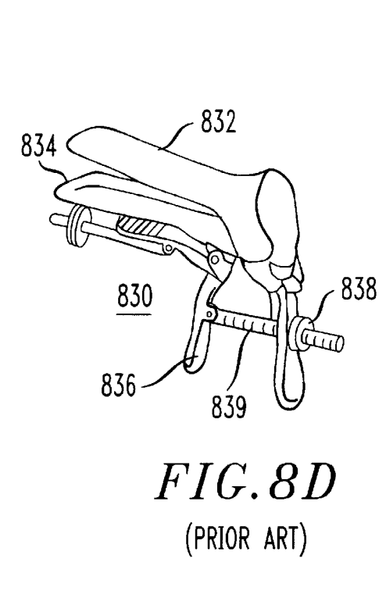

FIGS. 8a through 8d illustrate double billed (or bladed) vaginal specula. Referring first to FIGS. 8a and 8b, a double billed vaginal speculum 800/810 may include an upper bill or blade 802/812, a lower bill or blade 804/814, a lever 806/816 for moving the upper bill 802/812 with respect to the lower bill 804/814, and a threaded shaft 809/819 and set screw 808/818 for holding the lever 806/816 in position. As the outer surfaces of the bills separate the vaginal walls 112, the cervix 120 may be observed, and samples (biopsies) of cervical tissue or mucus may be taken, via opening 803. The vaginal speculum 820 of FIG. 8c is similar to those of FIGS. 8a and 8b in that it includes an upper bill 822, a lower bill 824, a lever 826, a threaded shaft 829, and a set screw 828, but differs in that the bills 822/824 are relatively perpendicular to the handle of the vaginal speculum 820. Finally, referring to FIG. 8d, a vaginal speculum 830 with a foldable handle (see phantom lines) is shown. The speculum 830 is similar to those of FIGS. 8a through 8c in that it includes an upper bill 832, a lower bill 834, a threaded shaft 839 and a set screw 838. However, in this case, the lever 836 actuates the lower bill 834 with respect to the upper bill 832. Each of the vaginal specula of FIGS. 8a through 8d permits two opposing sides of the vaginal wall 112 to be separated with one-hand. Moreover, once separated, the gynecologist can use the set screw 808/818/828/838, to maintain the opened position of the bills. However, since the handles of the vaginal specula 800/810/830 extend below the bills or blades, the center of gravity of each of these specula will be below the lower bill and towards the proximal end of the specula. Consequently, if such specula are not held in place, resulting moment arms between the vaginal contact points of the bills and the center of gravity, as well as the pliant nature of the vaginal walls 112, may cause the specula to droop within the vagina when released.

Figure 9:
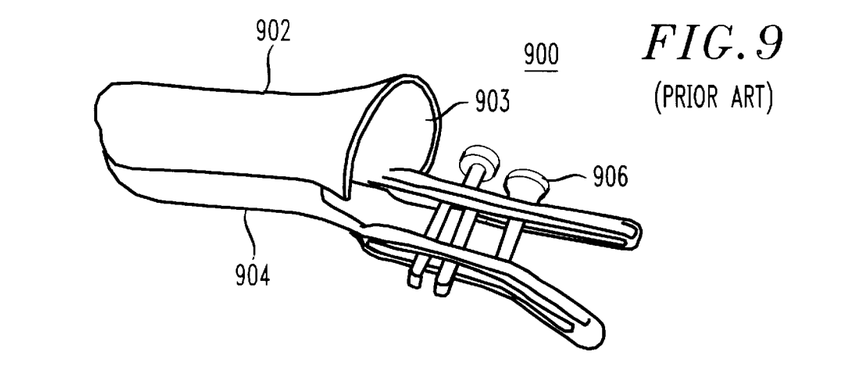
FIG. 9 illustrates a known double bladed or double billed vaginal specula.

Unfortunately, repositioning any of the double-billed vaginal specula of FIGS. 8a through 8d within the vagina 110 may cause discomfort, particularly since when separated, the upper and lower bills are angled with respect to one another. Referring to FIG. 9, the vaginal speculum 900 includes two set screws 906 which permit the upper and lower blades 902 and 904, defining opening to be opened while maintaining a parallel relationship with one another. In this way, repositioning the speculum 900 within the vagina 110 causes less patient discomfort.

Figure 10A:
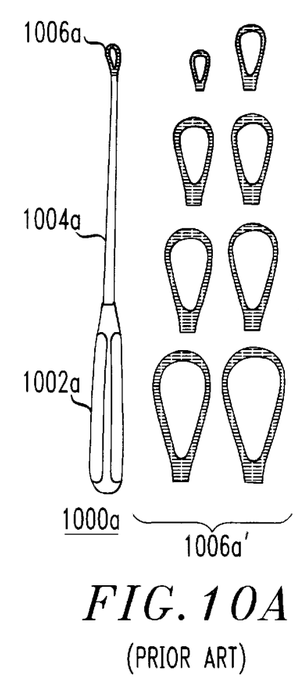
FIGS. 10a through 10c illustrate various known curettes with various blade types.
Figures 10B, 10C:
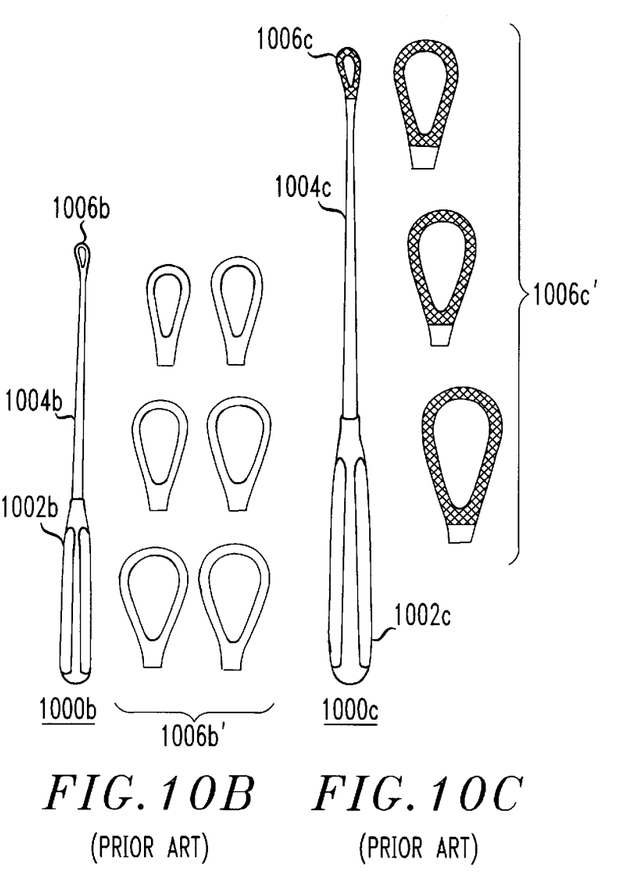

Curettes may be used, in conjunction with a vaginal speculum, to sample tissue or mucus of the vagina 110, cervix 120, and/or uterus 130. As shown in FIGS. 10a through 10c, the curettes 1000 typically include a handle 1002, a malleable shank 1004, and a blade 1006. The curette 1000a is provided with a sharp blade 1006a. Various sizes of the sharp blade 1006a' may be provided. The curette 1000b is provided with a blunt blade 1006b. Various sizes of the blunt blade 1006b' may also be provided. Finally, the curette 1000c is provided with a serrated blunt blade 1006c. Various sizes of the serrated blunt blade 1006c' may be provided.

§1.3 Use of Vaginal Specula

As discussed above, vaginal specula are used to separate the walls 112 of the vagina 110 during gynecological examinations and procedures. Often, a light is clamped to the proximal end of the specula and the gynecologist may examine the vagina 110, cervix 120, and/or uterus 130 for abnormal colors, growths (e.g., polyps), etc. Tissue and/or mucus samples or biopsies may be taken with the curette.

§1.4 Disadvantages of the Known Specula

Unfortunately, the known vaginal specula discussed above have a number of disadvantages. First, the bills of all of the specula discussed above include metal bills or blades. Since metal conducts heat, if the gynecologist's office is cold, the bills or blades will be cold, thereby causing patient discomfort when the cold bills or blades contact the relatively warm vaginal wall 112. Moreover, if a light is clipped to the distal end of a vaginal specula, the metal parts of the specula may conduct heat (or more dangerously electricity) from the light to the vagina 110. The use of vaginal specula with plastic bills or blades has overcome this problem to some extent. However, the plastic bills of such vaginal specula may not be as rigid as metal bills. Moreover, vaginal specula having plastic bills may include other disadvantages of known vaginal specula discussed below. In addition to providing a heat and/or electrical source which may cause problems with metal bills or blades as discussed above, if a light is clipped to the distal end of a vaginal specula, it may become contaminated by body fluids. In such cases, the light must either be cleaned (sterilized) or discarded.

The non-weighted one-bill specula of FIGS. 7a and 7b will occupy one of the gynecologist's hands, thereby making other procedures more difficult and awkward. Though the weighed one-bill specula of FIGS. 7c and 7d permit the gynecologist to free his or her hand by virtue of the weight and the angled bill, such specula are only useful for pulling the lower section of the vaginal wall 112 away from the upper section. Moreover, movement by the patient may cause these specula to fall out of the vagina.

§1.4.1 Advantages and Disadvantages of One-hand Specula

The double-billed specula of FIGS. 8a through 8d overcome some of the problems of the single-billed specula. However, patients may, experience discomfort, such as pinching or scraping for example, when the bills of the speculum are inserted and/or moved.

§1.4.2 Advantages and Disadvantages of Parallel Opening Blade Speculum

The vaginal speculum 900 of FIG. 9, which permits the bills to maintain a parallel relationship when opened, may alleviate some patient discomfort when the speculum is moved, but does not overcome patient discomfort occurring when the bills are initially inserted into the patient's vagina 110. Moreover, adjustments to the adjustable set screws 906 may be difficult and slow.

§1.4.3 Advantages and Disadvantages of the "Spruill" Speculum

U.S. Pat. No. 5,545,122 (hereafter referred to as "the Spruill patent") discusses a vaginal speculum having a pair of blades, each blade having a flexible expandable bladder. After the blades are inserted into the vagina, compressed gas is provided to the bladders to inflate them, thereby expanding the body cavity. The blades are plastic and relatively narrow. In this way, patient discomfort is reduced when the blades are initially inserted into the patient's vagina. Unfortunately, the construction of the vaginal speculum discussed in the Spruill patent (hereafter referred to as "the Spruill speculum") is relatively complicated. Thus, it is not believed that the Spruill device would be well suited as a disposable product. Accordingly, this device would have to be cleaned. Since it is believed that the inflatable bladders would not last as long as the hand and blades, these bladders would have to be replaced easily. It is not believed that the Spruill device adequately solves or addresses problems of manufacturing, cleaning, and/or part replacement.

SUMMARY OF THE INVENTION

In view of the problems with the specula discussed above, an improved specula is needed. It is a goal of the present invention to provide vaginal specula (and an accompanying system) which (i) minimizes patient discomfort, (ii) is easy and inexpensive to manufacture, (iii) is disposable, and (iv) facilitates gynecological examinations and/or procedures. The present invention provides an inflatable vaginal speculum having an inflatable bladder. The inflatable bladder (i) has a deflated state and an inflated state, (ii) is adapted for insertion into a vagina in the deflated state and for dilating walls of the vagina in the inflated state, (iii) defines a central channel when in the inflated state, and (iv) has an inlet/outlet port.

The vaginal speculum may also include optical fibers arranged with respect to the inflatable bladder. In this case, the inflatable bladder may be formed from a material having a cross section and the optical fibers may be embedded within the cross section of the material. Alternatively, the optical fibers may be attached to an outer surface of the inflatable bladder and/or an inner surface of the inflatable bladder. In yet another alternative embodiment, the optical fibers may be arranged within a void defined by the inflatable bladder.

The inflatable bladder has a proximal end and a distal end. More of the optical fibers may be provided at the distal end of the inflatable bladder than at the proximal end of the inflatable bladder. Similarly, distal tip ends of the optical fibers may be provided at the distal end of the inflatable bladder.

The vaginal speculum may also include a tube which is fitted into, and widens, the central channel of the inflatable bladder. The tube may be flared out at its end corresponding to the proximal end of the central channel. Optical fibers may be (a) embedded within the tube, (b) arranged on an inside surface of the tube, and/or (c) arranged on an outside surface of the tube.

The central channel of the inflatable bladder may have a proximal end and a distal end and the proximal end of the central channel may flare outward. When the inflatable bladder is in its inflated state, the distal end may include a longitudinal extension adapted to engage a cervix. The central channel of the inflatable bladder may be formed of less flexible material than remaining areas of the inflatable bladder such that it stretches less than the remaining areas upon inflation. Alternatively, or additionally, the central channel of the inflatable bladder may be formed thicker than remaining areas of the inflatable bladder such that it stretches less than the remaining areas upon inflation.

The inflatable bladder may be made from rubber, latex, or polyethylene.

An inflation device may be fluidly coupled with the inlet/outlet port of the inflatable bladder. The inflation device may be (a) a controllable, powered, pump, (b) a hand bulb, or (c) a controllable pressurized gas source.

A light source may be optically coupled with the optical fibers. The light source may include a 150 Watt white light source.

An outer surface and/or a channel surface of the inflatable bladder may be provided with a lubricant.

DETAILED DESCRIPTION

The present invention concerns novel methods and apparatus for facilitating gynecological examinations and procedures. The following description is presented to enable one skilled in the art to make and use the invention, and is provided in the context of particular specula, systems, and their requirements. Various modifications to the disclosed embodiments will be apparent to those skilled in the art, and the general principles set forth below may be applied to other embodiments and applications. Thus, the present invention is not intended to be limited to the embodiments shown.

§2. USES AND FUNCTIONS OF THE INVENTION

The objective of the present invention is to facilitate gynecological examinations and/or procedures while minimizing patient discomfort. In particular, the objective of the present invention is to provide inflatable specula for separating the walls of the vagina so that the cervix and/or uterus may be examined, treated, and/or operated on. The inflatable specula should be relatively inexpensive and easy to manufacture, such that they are viable as disposable devices.

§3. FIRST EMBODIMENT (CLEAR PLASTIC INSERTION TUBE WITH FOOTBALL SHAPED BLADDER)

§3.1 Structure of First Embodiments

Figure 4:
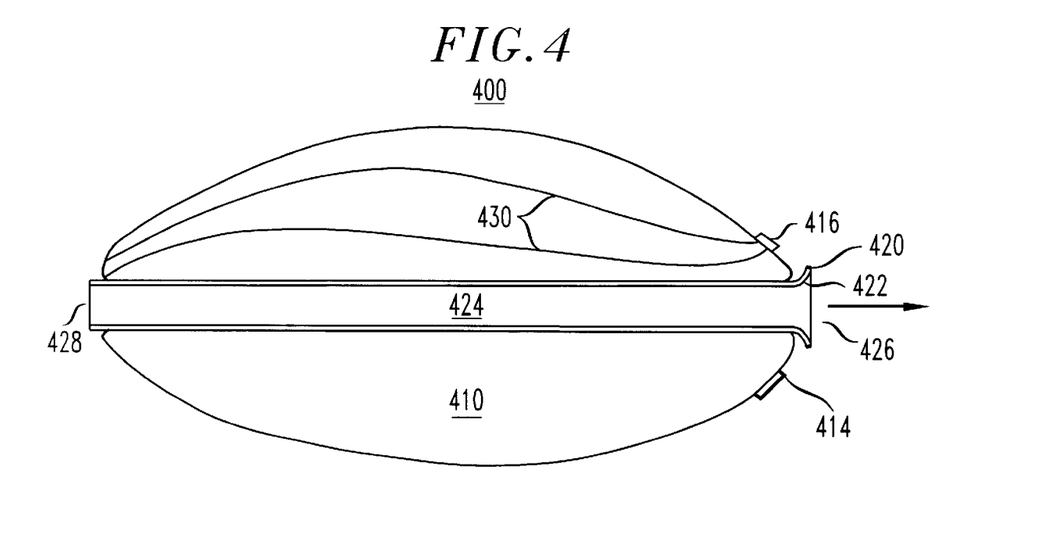
FIG. 4 is a partial cross-sectional side view of yet another embodiment of a vaginal speculum made in accordance with the present invention.

FIG. 4 is a partial cross-sectional side view of a first embodiment of an inflatable vaginal speculum 400 made in accordance with the present invention. The inflatable speculum 400 includes an inflatable bladder 410 which surrounds a cylindrical tube 424. A gas inlet/outlet interface 414 is provided on a proximal end of the inflatable bladder 410 of the speculum 400. The inflatable bladder 410 is formed from flexible material, such as rubber, latex, or polyethylene for example. The tube 424 may be formed of a relatively rigid material, such as a plastic, and is preferably clear. The tube 424 includes a distal end opening 428 and a proximal end opening 426. The tube 424 may be flared out 422 at its proximal end opening 426 to facilitate the insertion of medical tools such as curettes, endoscope insertion tubes, etc. Although endoscopes are known to those skilled in the art, a brief description of an endoscope is provided for the reader's convenience.

Figure 11:
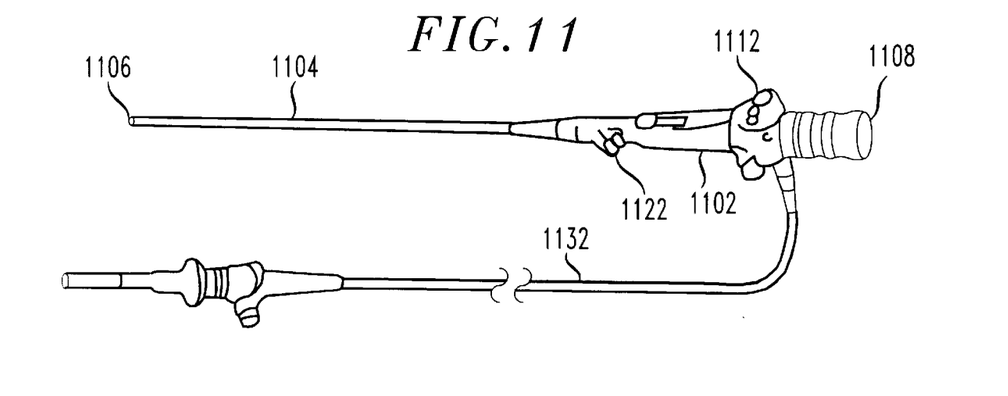
FIG. 11 depicts a hysterofiberscope which may be used with the present invention to examine or treat the uterus.

FIG. 11 illustrates a hysteroscope 1100 which may be used to observe and take samples from the uterus 130. The hysteroscope 1100 includes a body 1102 and an insertion tube 1104. The distal end 1106 of the insertion tube 1104 may include a lens, illumination means, and a working channel port. An image acquired at the distal end 1106 of the insertion tube 1104 is carried by optical fibers to an eyepiece 1108. The distal end 1106 of the insertion tube 1104 may be articulated by control knob 1112. A suction/insufflation port 1122 is also provided. Finally, a light guide 1132 may carry light from a light source (not shown) to the body 1112 of the hysteroscope 1100. Light guides (not shown) then convey the light from the body 1112 to the illumination means at the tip at the distal end 1106 of the insertion tube 1104 of the hysteroscope 1100.

Figure 5A:
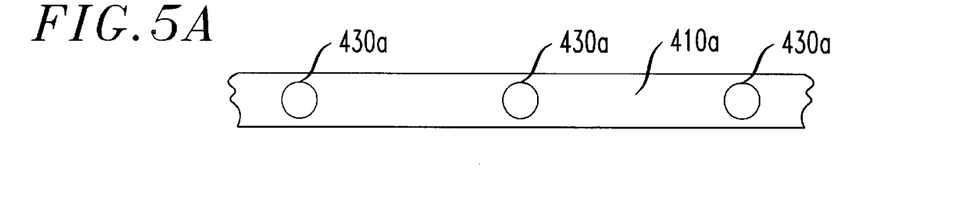
FIGS. 5a through 5e depict cross-sections of various arrangements of an inflatable bladder and optical fibers.
Figure 5B:
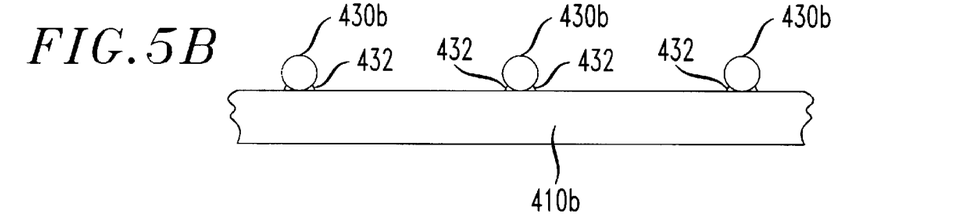
Figure 5C:
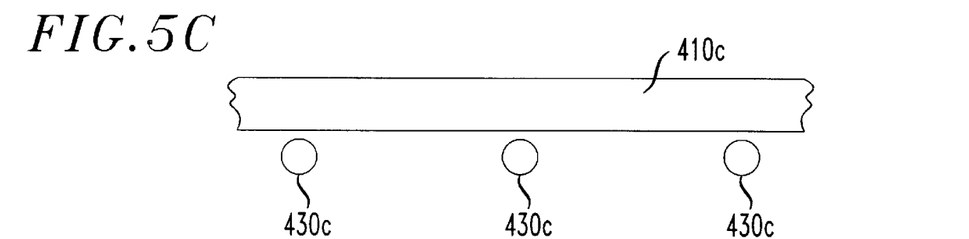
Figure 5D:
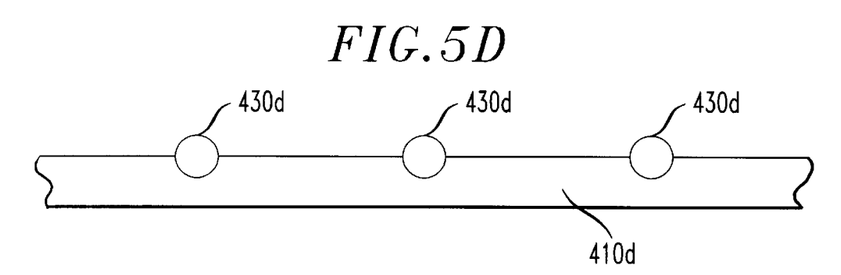
Figure 5E:
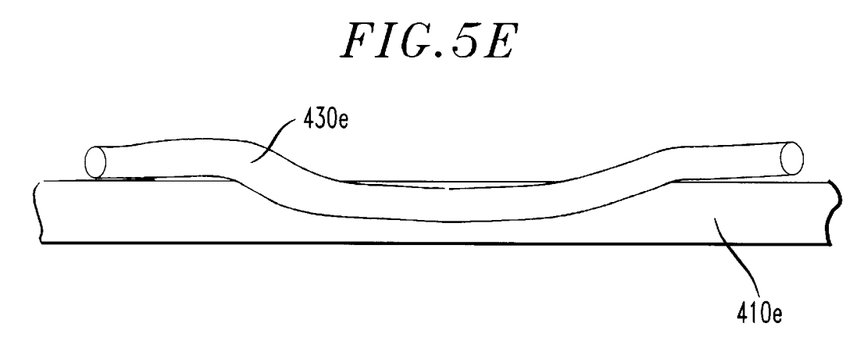
Figure 6:
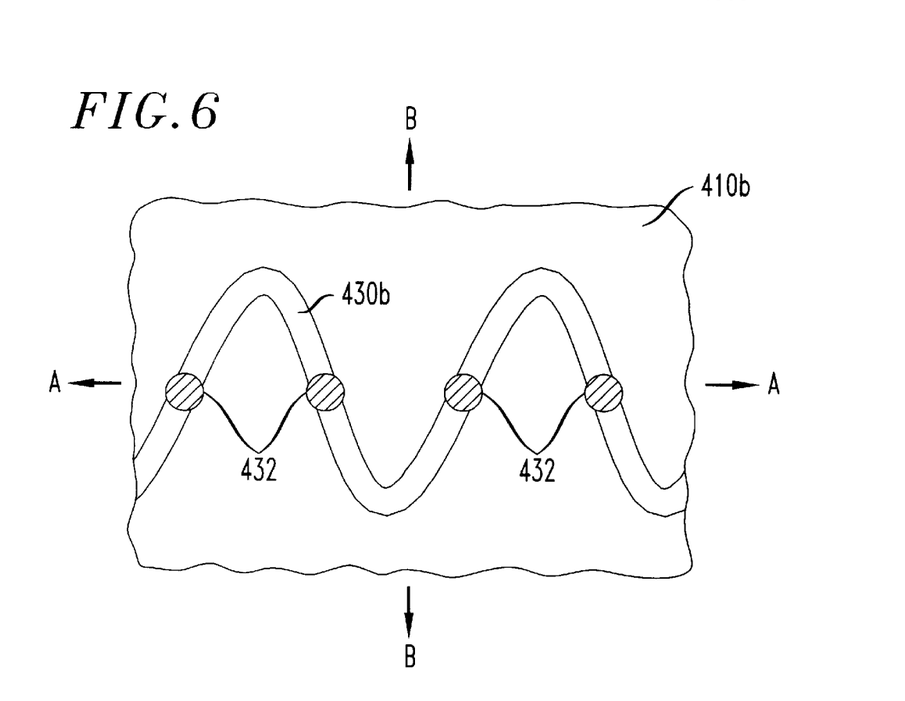
FIG. 6 is a plan view depicting an attachment of an optical fiber to the inner or outer surface of an inflatable bladder.

The speculum 400 of the present invention may be provided with optical fibers 430 for illuminating the vaginal walls 112 and/or cervix 120. A light source connector 416 is provided at the proximal end of the inflatable bladder 410 of the speculum 400 so that the optical fibers 430 may be optically coupled with an external light source (not shown). Referring to FIG. 5a, the optical fibers 430a may be imbedded within the material of the inflatable bladder 410a. Referring to FIG. 5b, the optical fibers 430b may alternatively be attached to the inside and/or outside surface of the inflatable bladder 410b. Adhesive 432 may be used to adhere the optical fibers 430b to the inflatable bladder 410b. As shown in the plan view of FIG. 6, the optical fiber 430b may be arranged in a serpentine manner and adhered to the inflatable bladder 410b at points 432. In this way, when the inflatable bladder 410b is inflated and expands as shown by the arrows A and B, the optical fiber 430b will straighten. Thus, the fact that the inflatable bladder 410b will expand and contract more than the optical fiber 430b is accounted for. As shown in FIGS. 5d and 5e, the optical fibers 430 may be partially embedded (cross-section wise or length wise) in the inflatable bladder 410 such that they partially extend out from the bladder 410. Finally, as shown in FIG. 5c, the optical fibers 430c may be provided within, but not attached to, the bladder 410c. This arrangement also accounts for the fact that the inflatable bladder 410c will expand and contract more than the optical fibers 430c.

Alternatively or additionally, optical fibers may be provided on (e.g., adhered to) the inner surface of the tube 424, provided on (e.g., adhered to) the outer surface of the tube 424, embedded within the tube 424 or partially embedded in the tube 424.

The bulk of the optical fiber(s) may be concentrated at the distal end of the inflatable bladder 410 (or tube 424) so that the cervix 120 is adequately illuminated. The optical fiber(s) may emit more light from its distal tip end(s) than its surfaces. Thus, the distal tip end(s) of the optical fiber(s)

may be concentrated at the distal end of the inflatable bladder 410 (or tube 424) so that the emitted light is directed towards the cervix 120.

Although the inflatable bladder 410 is depicted as having a football shape, it may take on other shapes such as substantially cylindrical.

§3.2 Operation of First Embodiment

The first embodiment of the inflatable speculum 400 operates as follows. The tube 424, along with the deflated bladder 410 is inserted into the patient's vagina 110. The outer wall of the bladder 410 may be pre-lubricated or may be provided with a lubricant to facilitate its insertion. Once in place, gas is provided to the bladder 410 via gas inlet/outlet port 414. The gas may be provided by an external source such as a controllable pressurized gas source, a controllable, powered, pump, or a hand bulb. The use of a hand bulb would provide the attending gynecologist with a good tactile feel for the air pressure within the bladder 410. Consequently, the bladder 410 is inflated, preferably under the control of the attending gynecologist.

If optical fibers 430 are provided, they may be optically coupled with a light source (not shown) via connector 416 to illuminate the vaginal cavity 110 and/or cervix 120. A curette may be passed from the proximal end 426 of the tube 424 and out through the distal end 428 of the tube 424 for purposes of taking a tissue or mucus sample of the cervix 120 or uterus 130. In addition, the insertion tube (See, e.g., 1104 of FIG. 11) of an endoscope, such as a hysteroscope (See, e.g., 1100 of FIG. 11) for example, may be passed from the proximal end 426 of the tube 424 and out through the distal end 428 of the tube 424 and the cervix 120 for purposes of examining the uterus 130.

When the examination and/or procedure is complete, the bladder 410 is deflated and the speculum 400 is removed.

It is possible to provide the tube 424 separate from the rest of the inflatable speculum 400. In this case, the tube 424 may be inserted after the bladder 410 has been inserted into the vaginal cavity 110 and inflated. The tube 424 may serve to enlarge the inner channel defined by the inflated bladder 410. The inner diameter of the tube 424 should be large enough such that a curette may pass through it.

§4. SECOND EMBODIMENT (THICKER, MORE RIGID BLADDER)

§4.1 Structure of Second Embodiment

Figure 2:
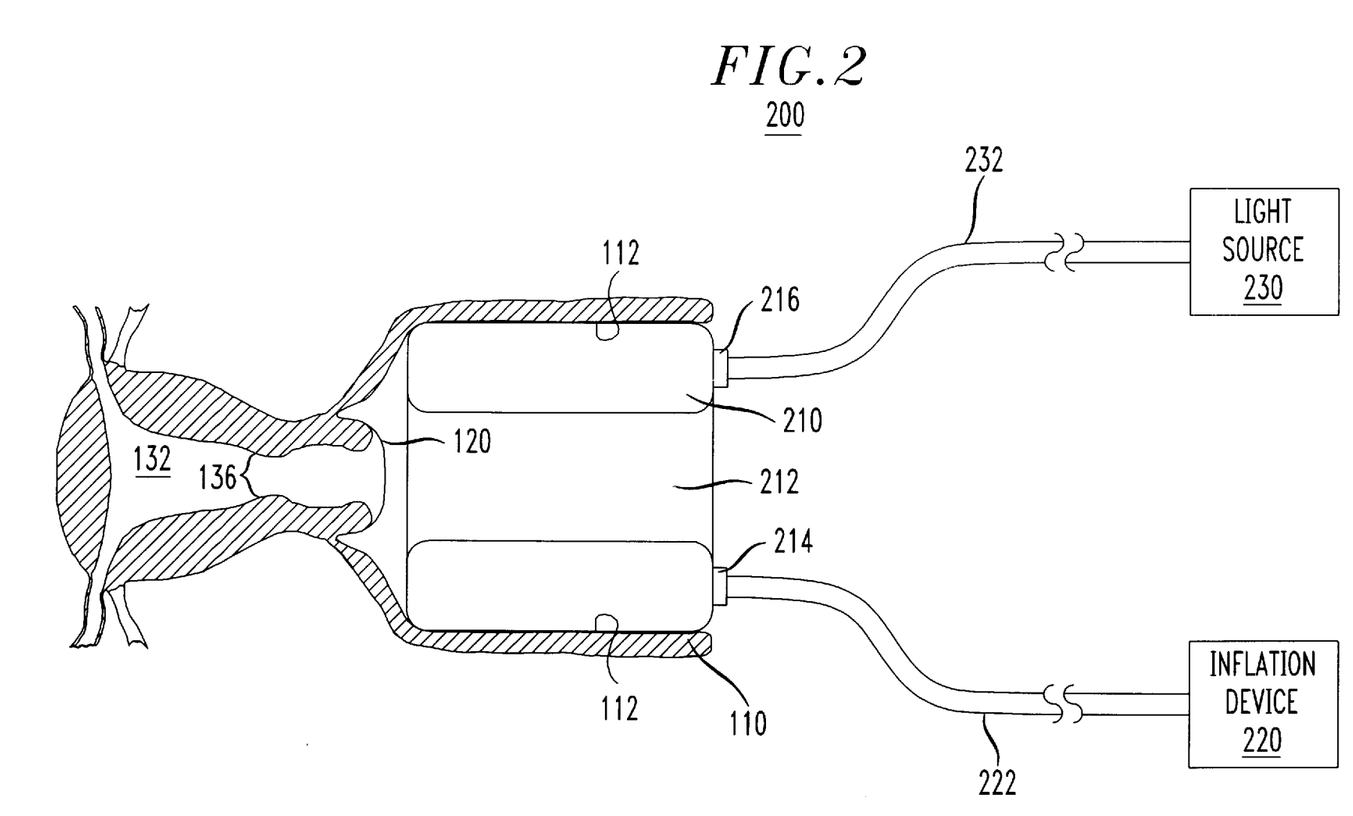
FIG. 2 is a partial cross-sectional illustration of an embodiment of a system of the present invention used to separate vaginal walls 112 during a gynecological examination and/or procedure.

FIG. 2 is a partial cross-sectional illustration of a second embodiment of a system 200 of the present invention used to separate vaginal walls 112 during a gynecological examination and/or procedure. The system includes an inflatable bladder 210 formed of a flexible material, such as rubber, latex, polyethylene, etc., for example. The inflatable bladder 210, when inflated as shown, takes on a cylindrical shape which defines a central void 212. The inner walls of the inflatable bladder 210 may be formed of a thicker and/or tougher material than that of the outer walls. The outer walls of the inflatable bladder 210 separate the walls 112 of the vagina 110. An inflation device (e.g., a controllable source of compressed gas, a controllable powered pump, or a hand bulb) 220 is coupled with the inflatable bladder 210 via tube 222 and gas inlet/outlet port 214.

If the inflatable bladder 210 is provided with optical fibers as discussed above with reference to FIGS. 4 through 6, a light source 230 (e.g., a 150 Watt white light bulb) may be optically coupled with the optical fibers via optical connectors 232 and optical connector 216. The bulk of the optical fibers may be concentrated at the distal end of the inflatable bladder 210 so that the cervix 120 is adequately illuminated. The optical fibers may emit more light from their distal tip ends than their other surfaces. Thus, the distal tip ends of the optical fibers may be concentrated at the distal end of the inflatable bladder 210 so that the emitted light is directed towards the cervix 120.

The bladder 210 may be shaped so that the diameter of the central void 212 is a relatively large portion of the diameter of the inflated bladder 210. This objective may be met by (a) appropriately shaping the bladder 210, and/or (b) forming the inner (channel) surface of the bladder 210 of thicker or less flexible material than the outer surface of the bladder 210 so that when the bladder is inflated, the inward expansion of the inner walls will be less than the outward expansion of the outer walls.

Though not shown, the inflatable bladder 210 may be provided with a rigid tube which performs functions similar to those performed by the tube 424 of FIG. 4.

§4.2 Operation of Second Embodiment

As shown in FIG. 2, using the system 200, the cervix 120 may be examined. More specifically, a (lubricated) deflated bladder 210 is inserted into the vaginal cavity 110. The inflation device 220 then provides gas to the bladder 210 via the tube 222 and gas inlet/outlet port 214. The provision of gas may be controlled by the attending gynecologist so that the rate and extent of inflation of the bladder 210 is controlled to minimize discomfort to the patient. When the bladder 210 is inflated, the cervix 120 may be examined and cervical tissue or mucus may be taken using a curette. If optical fibers are provided, the light source 230 may be activated to illuminate the vaginal cavity 110 in general, and the cervix 120 in particular. When the examination and/or procedure is done, the light source may be switched off and the bladder 210 may be deflated and removed from the vagina 110.

§5. THIRD EMBODIMENT (CONTOURED BLADDER FOR USE WITH HYSTEROSCOPE)

The first 400 and second 200 embodiments of the present invention are particularly well suited to facilitate examination of, and procedures to, the cervix 120. A third embodiment will now be described which is particularly well-suited for the examination of, and procedures to, the uterus 130.

§5.1 Structure of Third Embodiment

Figure 3:
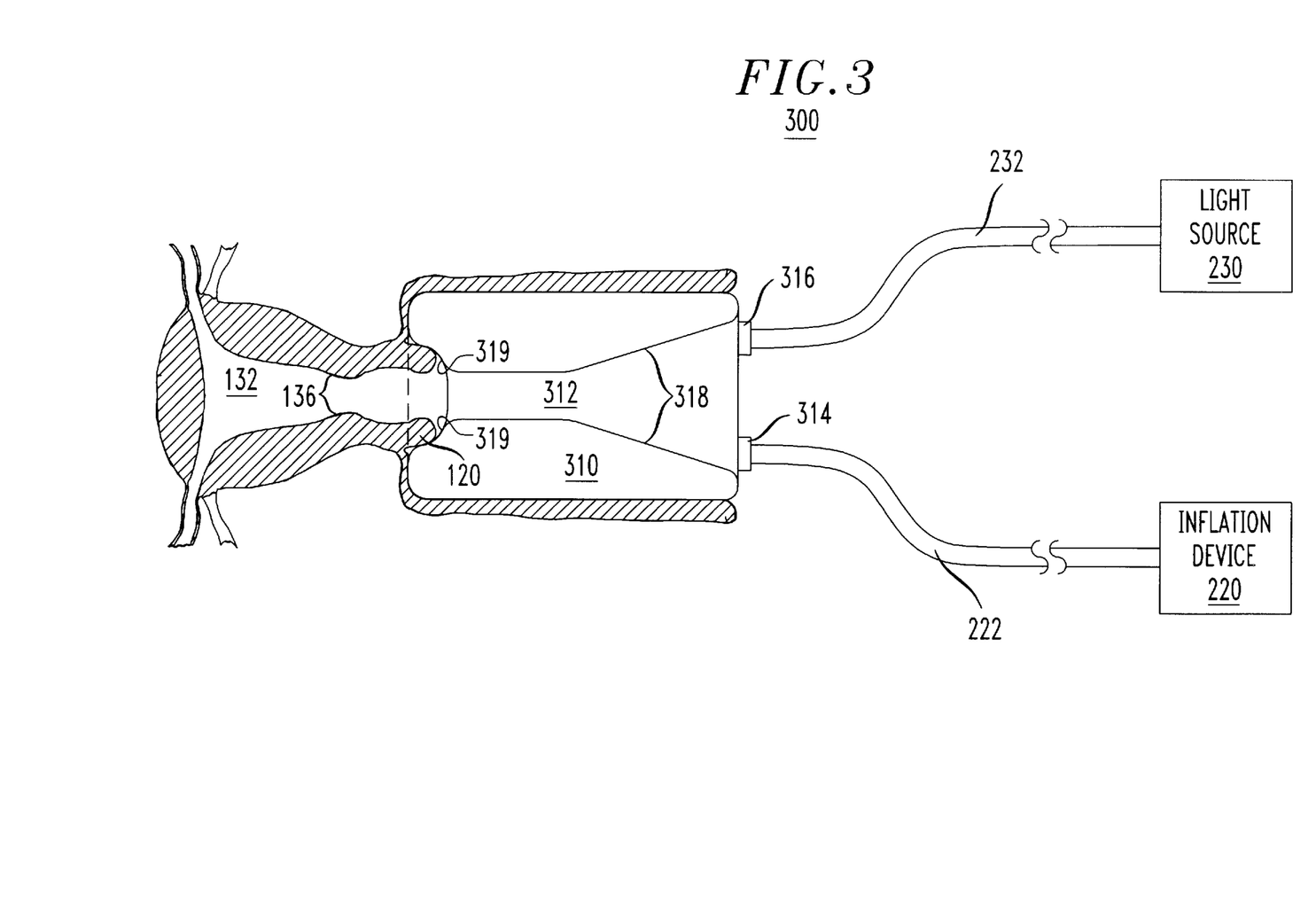
FIG. 3 is a partial cross-sectional illustration of another embodiment of a system of the present invention used to separate vaginal walls 112 during a gynecological examination and/or procedure.

FIG. 3 is a partial cross-sectional illustration of the third embodiment of a system 300 of the present invention used to separate vaginal walls 112 during a gynecological examination and/or procedure. In the system 300 of FIG. 3, the inflatable bladder 310 inflates to a preformed shape which is contoured to the vagina 110 and cervix 120. More specifically, the inflatable bladder 310 inflates to a preformed shape having a distal surface 319 which conforms to the shape of, and thus engages, the cervix 120. A central opening 312 of the bladder 310 includes an outwardly flared proximal end 318. As was the case with the bladder 210 of the second embodiment discussed above with reference to FIG. 2, the inner portion 312 of the bladder 310 may be made from thicker and/or less flexible material than that of the outer portions of the bladder 310. The bladder 310 includes a gas inlet/outlet port 314. If optical fibers are provided (See e.g., FIGS. 4 through 6), the bladder 310 may be provided with a light source connector 316. An inflation device (e.g., a controllable compressed gas source, a powered controllable pump, or a hand bulb) 220 may be coupled with the gas inlet/outlet port 314 via tube 222. A light source 230 may be coupled with the optical connector 316 via light guide 232.

Though not shown, the inflatable bladder 210 may be provided with a rigid tube which performs functions similar to those performed by the tube 424 of FIG. 4.

§5.2 Operation of Third Embodiment

As alluded to above, the third embodiment 300 of the present invention is particularly well suited for uterus 130 examinations and procedures. More specifically, the (lubricated) bladder 310 is inserted into the vagina 110 in a deflated state. The bladder 310 is then at least partially inflated with inflation device 220. The partially inflated bladder 310 is then positioned so that the extending outer portions of its distal end extend into the region between the outer diameter of the cervix 120 and the vaginal walls 110. The bladder 310 is then more fully inflated.

If optical fibers (not shown) are provided, the light source 230 may be switched on so that the vagina 110, cervix 120, and/or uterus 130 are illuminated.

Once the bladder 310 is inflated, the insertion tube of an endoscope (See, e.g., 1104 of FIG. 11), such as a hysteroscope (See, e.g., 1100 of FIG. 11) for example, may be passed through the central opening 312 of the bladder 310 and into the uterus 130. The flared-out portion 318 of the central opening 312 of the bladder facilitates the insertion of the endoscope insertion tube. In addition, the central opening may be provided with a lubricant to facilitate the insertion of the endoscope insertion tube. Once within the uterus 130, illumination means at the distal end of the insertion tube of the endoscope may be used to illuminate the walls 136 of the uterus 130. Images of the walls 136 of the uterus are acquired at the distal end of the endoscope (See, e.g., 1106 of FIG. 11) and passed (either optically, or as video signals) to the proximal end (See, e.g., 1108 of FIG. 11) of the endoscope. Small curettes, biopsy forceps (snare or jaw-type), or cannula may be passed through a working channel of the endoscope so that tissue or mucus samples of the uterus 130 (or of the contents of the uterus), may be taken. When the examination of, and/or procedure to, the uterus 130 is complete, the bladder 310 may be deflated and removed.

Although the inflatable bladders 210/310/410 where described as being inflated with gas from an inflation device, a liquid fluid, such as water or a saline solution for example, may be used to expand the bladder. If such a liquid fluid is used, it should be kept at a temperature close to that of the vagina.

Figure 12A:
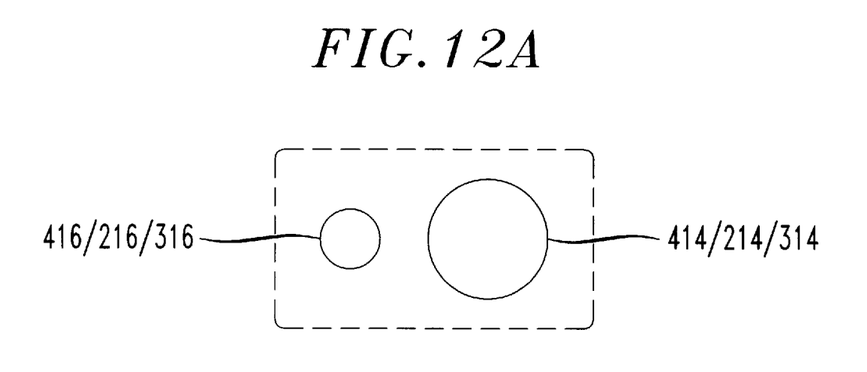
FIGS. 12a through 12c depict cross-sections of various gas/light guide connection arrangements which may be used in the vaginal specula of FIGS. 2 through 4.
Figure 12B:
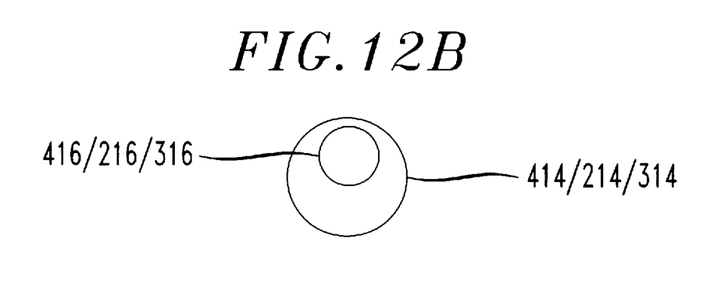
Figure 12C:
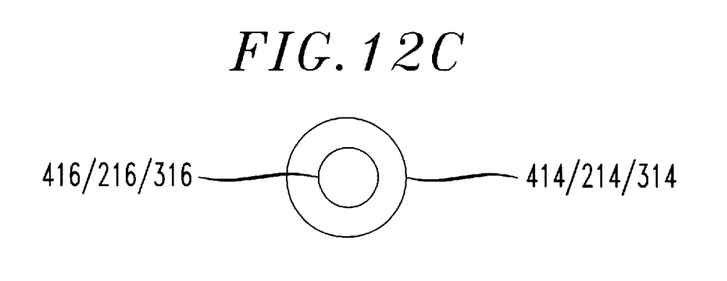

Although the light guide connectors 416/216/316 were shown as being physically separated from the gas inlet/outlet ports 414/214/314, the light guide connectors and inlet/outlet ports may be arranged in close proximity to one another (as shown in the cross section of FIG. 12a), or one within the other (as shown in the cross sections of FIGS. 12b and 12c) such that both may receive a one-piece combined light source/gas source connector. In this way, use of the vaginal specula of the resent invention is simplified.

§6. SUMMARY

In view of the above, the present invention provides improved methods and apparatus for examining both the cervix and the uterus and for facilitating gynecological procedures.

What is claimed is:
1. A vaginal speculum comprising:
    a) an inflatable bladder, the inflatable bladder
        i) having a deflated state and an inflated state,
        ii) being adapted for insertion into a vagina in the deflated state and for dilating walls of the vagina in the inflated state,
        iii) defining a central channel when in the inflated state, and
        iv) having an inlet/outlet port; and
    b) optical fibers
    wherein the inflatable bladder is formed from a material having a cross section and
        wherein the optical fibers are arranged with respect to the inflatable bladder in an arrangement selected from a group of arrangements consisting of: (a) embedded within the cross section of the material; (b) attached to an outer surface of the inflatable bladder; (c) attached to an inner surface of the inflatable bladder; and (d) arranged within a void defined by the inflatable bladder.

2. The vaginal speculum of claim 1 wherein the inflatable bladder has a proximal end and a distal end, and wherein more of the optical fibers are provided at the distal end of the inflatable bladder than at the proximal end of the inflatable bladder.

3. The vaginal speculum of claim 1 wherein the inflatable bladder has a proximal end and a distal end, and wherein distal tip ends of the optical fibers are provided at the distal end of the inflatable bladder.

4. A vaginal speculum comprising:
    a) an inflatable bladder, the inflatable bladder
        i) having a deflated state and an inflated state,
        ii) being adapted for insertion into a vagina in the deflated state and for dilating walls of the vagina in the inflated state,
        iii) defining a central channel when in the inflated state, and
        iv) having an inlet/outlet port;
    b) a tube which is fitted into, and widens, the central channel of the inflatable bladder; and
    c) optical fibers arranged in at least one location selected from a group consisting of (a) embedded within the tube, (b) on an inside surface of the tube, and (c) on an outside surface of the tube.

5. The vaginal speculum of claim 4 further comprising a light source optically coupled with the optical fibers.

6. The vaginal speculum of claim 5 wherein the light source includes a 150 Watt white light source.

7. A vaginal speculum comprising:
    a) an inflatable bladder, the inflatable bladder
        i) having a deflated state and an inflated state,
        ii) being adapted for insertion into a vagina in the deflated state and for dilating walls of the vagina in the inflated state,
        iii) defining a central channel when in the inflated state, and
        iv) having an inlet/outlet port,
    wherein the central channel has a proximal end and a distal end, and wherein the proximal end of the central channel flares outward.

8. The vaginal speculum of claim 7 wherein, when the inflatable bladder is in its inflated state, the distal end includes a longitudinal extension adapted to engage a cervix.

9. A vaginal speculum comprising:
    a) an inflatable bladder, the inflatable bladder
        i) having a deflated state and an inflated state, ii) being adapted for insertion into a vagina in the deflated state and for dilating walls of the vagina in the inflated state,
iii) defining a central channel when in the inflated state, and
iv) having an inlet/outlet port, wherein the inflatable bladder has a proximal end and a distal end, and wherein, when the inflatable bladder is in its inflated state, the distal end includes a longitudinal extension adapted to engage a cervix.

10. A vaginal speculum comprising:
    a) an inflatable bladder, the inflatable bladder
        i) having a deflated state and an inflated state,
        ii) being adapted for insertion into a vagina in the deflated state and for dilating walls of the vagina in the inflated state,
        iii) defining a central channel when in the inflated state, and
        iv) having an inlet/outlet port,
wherein the central channel of the inflatable bladder is formed of less flexible material than remaining areas of the inflatable bladder such that it stretches less than the remaining areas upon inflation.

11. The vaginal speculum of claim 10 wherein the central channel of the inflatable bladder is formed thicker than remaining areas of the inflatable bladder such that it stretches less than the remaining areas upon inflation.

12. A vaginal speculum comprising:
    a) an inflatable bladder, the inflatable bladder
        i) having a deflated state and an inflated state,
        ii) being adapted for insertion into a vagina in the deflated state and for dilating walls of the vagina in the inflated state,
        iii) defining a central channel when in the inflated state, and
        iv) having an inlet/outlet port,
wherein the central channel of the inflatable bladder is formed thicker than remaining areas of the inflatable bladder such that it stretches less than the remaining areas upon inflation.

13. A vaginal speculum comprising:
    a) an inflatable bladder, the inflatable bladder
        i) having a deflated state and an inflated state,
        ii) being adapted for insertion into a vagina in the deflated state and for dilating walls of the vagina in the inflated state,
        iii) defining a central channel when in the inflated state, and
        iv) being formed solely of a flexible material; and
    b) a tube which extends through the central channel of the inflatable bladder.

14. The vaginal speculum of claim 13 wherein the central channel of the inflatable bladder has a proximal end and a distal end, and wherein the tube is flared out at its end corresponding to the proximal end of the central channel.

15. The vaginal speculum of claim 13 wherein the inflatable bladder is made from a material selected from a group consisting of (a) rubber, (b) latex, and (c) polyethylene.

16. The vaginal speculum of claim 13 further comprising an inflation device fluidly coupled with an inlet/outlet port of the inflatable bladder.

17. The vaginal speculum of claim 16 wherein the inflation device is selected from a group consisting of (a) a controllable, powered, pump, (b) a hand bulb, and (c) a controllable pressurized gas source.

18. The vaginal speculum of claim 13 wherein at least one of an outer surface and a channel surface of the inflatable bladder is provided with a lubricant.

19. A vaginal speculum comprising:
    a) an inflatable bladder, the inflatable bladder
        i) having a deflated state and an inflated state,
        ii) being adapted for insertion into a vagina in the deflated state and for dilating walls of the vagina in the inflated state, and
        iii) defining a central channel when in the inflated state, the central channel being formed by a flexible material; and
    b) a tube which extends through the central channel of the inflatable bladder.

* * * * *